United States Patent [19]

Effenberger et al.

[11] 4,456,766

[45] Jun. 26, 1984

[54] PROCESS FOR THE PRODUCTION OF N-ACETYL-2,3-DEHYDRO-AMINOCARBOXYLIC ACID ESTERS

[75] Inventors: Franz Effenberger; Thomas Beisswenger, both of Stuttgart, Fed. Rep. of Germany

[73] Assignee: Degussa Aktiengesellschaft, Frankfurt am Main, Fed. Rep. of Germany

[21] Appl. No.: 418,843

[22] Filed: Sep. 16, 1982

[30] Foreign Application Priority Data

Oct. 9, 1981 [DE] Fed. Rep. of Germany ....... 3140227

[51] Int. Cl.$^3$ ................ C07C 102/04; C07C 103/127; C07C 149/23; C07C 149/31
[52] U.S. Cl. ......................................... 560/17; 560/41; 560/153; 560/172; 560/155; 562/431; 562/450; 562/575
[58] Field of Search .................... 560/172, 153, 41, 17

[56] References Cited

FOREIGN PATENT DOCUMENTS

| 500358 | 3/1954 | Canada | 560/41 |
|---|---|---|---|
| 595319 | 3/1960 | Canada | 560/41 |
| 1946550 | 3/1971 | Fed. Rep. of Germany | 560/41 |
| 119414 | 9/1979 | Japan | 560/41 |
| 26821 | 3/1981 | Japan | 560/41 |
| 547443 | 7/1977 | U.S.S.R. | 560/41 |

OTHER PUBLICATIONS

Hilgetag, ed., *Preparative Organic Chemistry*, John Wiley and Sons, New York, 1972, pp. 1081–1082.
*Angew. Chem. Int. Ed. Engl.*, vol. 21, No. 3, p. 203 (1982); Effenberger et al.
Manis, J. Org. Chem. vol. 45 (1980), pp. 4952–4954.

*Primary Examiner*—Natalie Trousof
*Assistant Examiner*—Patricia M. Scott
*Attorney, Agent, or Firm*—Cushman, Darby & Cushman

[57] ABSTRACT

The subject matter of the invention is a process for the production of N-acetyl-2,3-dehydroaminocarboxylic acid esters by reaction of the corresponding 2-azidocarboxylic acid esters with a mixture of one part by volume of acetic anhydride and 1.5 to 5 parts by volume of acetic acid in the presence of rhenium VII sulfide and/or oxide and at a temperature between 50° and 150° C., in a given case, in the simultaneous presence of dry hydrogen chloride.

20 Claims, No Drawings

PROCESS FOR THE PRODUCTION OF N-ACETYL-2,3-DEHYDRO-AMINOCARBOXYLIC ACID ESTERS

BACKGROUND OF THE INVENTION

The subject matter of the invention is a new process for the production of N-acetyl-2,3-dehydro-aminocarboxylic acid esters of the general formula:

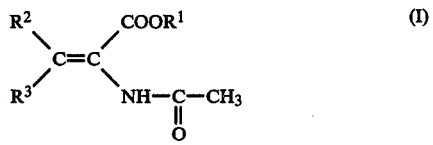

in which $R^1$ is a methyl or ethyl group, $R^2$ is hydrogen or a methyl group and $R^3$ is hydrogen, an alkyl group having 1 to 6 carbon atoms, an aryl group, an unsubstituted or substituted alkylmercapto group, e.g. the alkyl group has 1 to 6 carbon atoms, or an arylmercapto group.

Compounds of the general formula (I) are known. They serve chiefly as intermediate products for the production of optically active 2-N-acetylaminocarboxylic acids by asymmetrical catalytic hydrogenation of the prochiral C=C double bond.

It is also known already to produce N-acetyl-2,3-dehydro-aminocarboxylic acid esters in a two-step process by reaction of 2-azido-carboxylic acid esters with n-butyl-lithium/ethanol and subsequent acylation with acetyl chloride, (Manis et al, J. Org. Chem. Vol. 45 (1980), pages 4952-4954). In this manner there can be produced, for example, the N-acetyl-2,3-dehydro-alanine ethyl ester in a yield of 58% of theory.

SUMMARY OF THE INVENTION

The process of the invention is characterized by reacting a 2-azido-carboxylic acid ester of the general formula:

in which $R^1$, $R^2$, and $R^3$ are as defined above, in the presence of rhenium VII sulfide and/or oxide and at a temperature between 50° and 150° C. with a mixture of one part by volume acetic anhydride and 1.5 to 5 parts by volume of acetic acid.

In this way it is possible to produce the desired N-acetyl-2,3-dehydro-aminocarboxylic acid ester of general formula (I) in a single step process easily and in high yield.

Examples of 2-azido-carboxylic acid esters of general formula (II) which can be reacted according to the process of the invention are, among others, the methyl and ethyl ester of 2-azido-propionic acid, 2-azido-butyric acid, 2-azido-3-methyl-butyric acid, 2-azido-3-phenyl-propionic acid, 2-azido-valeric acid, 2-azido-hexanoic acid, 2-azido-heptanoic acid, 2-azido-3-methylmercapto-propionic acid, 2-azido-3-methoxycarbonylmethylmercapto-propionic acid, 2-azido-nonanoic acid, 2-azido-8-methyl-nonanoic acid, 2-azido-3-ethyl-mercapto-propionic acid and 2-azido-3-hexylmercapto-propionic acid.

The rhenium VII sulfide and/or oxide serving as catalyst is used suitably in an amount between 0.01 and 10 mole percent based on the 2-azidocarboxylic acid ester of general formula (II) employed. The especially preferred amounts in the case of rhenium VII sulfide lie between 0.5 and 2 mole percent and in the case of rhenium VII oxide between 0.05 and 1 mole percent.

The process of the invention is preferably carried out at a temperature between 60° and 90° C. In order to avoid loss of yield through polymerization of the N-acetyl-2,3-dehydro-aminocarboxylic acid ester of general formula (I) formed, it is suitable to carry out the reaction in the presence of a known inhibitor for radical polymerization, such as hydroquinone or hydroquinone monomethyl ether. The inhibitor can be employed in an amount of 0.001 to 10 weight percent, especially 0.1 to 2.5 weight percent, based on the 2-azido-carboxylic acid ester of general formula (II) employed.

The mixture of one part by volume of acetic anhydride and 1.5 to 5 parts by volume of acetic acid serving as acetylation agent is suitably used in an amount of 260 to 5000 ml, preferably 500 to 3000 ml per mole of 2-azido-carboxylic acid ester of general formula (II) employed.

The process of the invention for example can be carried out in such manner that a mixture of acetic anhydride and acetic acid with the rhenium VII sulfide and/or oxide and, in a given case, the polymerization inhibitor is present and with vigorous stirring the 2-azidocarboxylic acid ester of the general formula (II) which is to be reacted is fed in slowly, e.g. in the course of two hours. It is recommended to maintain the reaction mixture at the reaction temperature after the end of the development of nitrogen for a longer period of time, for example 20 hours.

A considerable shortening of the required reaction time can be attained in many cases if the reaction is undertaken in the simultaneous presence of dry hydrogen chloride. In this case, it is advantageous to dissolve the 2-azido-carboxylic acid ester of general formula (II) which is to be reacted in the mixture of acetic anhydride and acetic acid, to add the rhenium VII sulfide and/or oxide and, in a given case, the polymerization inhibitor and then to lead in dry hydrogen chloride up to saturation. Then the mixture is subsequently heated to the reaction temperature. Generally in this method of operation a reaction time of at most 3 hours is sufficient.

After the end of the reaction the acetic acid and the excess acetic anhydride are removed, suitably under reduced pressure, for example, in a rotary evaporator. The residue is taken up in a readily volatile solvent, for example, diethyl ether, the solution filtered and the filtrate evaporated under reduced pressure. For further purification the residue is then chromatographed over a silica gel column with a mixture of low boiling petroleum ether and ethyl acetate (volume ratio about 2:1) as the mobile phase. After evaporation of the eluate, suitably again under reduced pressure, there remains behind the practically analytically pure N-acetyl-2,3-dehydro-aminocarboxylic acid of general formula (I).

Then by asymmetrical catalytic hydrogenation in known manner at will, there can be produced the corresponding L- or D-N-acetyl-aminocarboxylic acid esters from the N-acetyl-2,3-dehydro-aminocarboxylic acid esters, and the L- or D-N-acetyl-aminocarboxylic acid esters saponified to the corresponding L- or D-2-aminocarboxylic acids.

Unless otherwise indicated all parts and percentages are by weight.

The process can comprise, consist essentially of, or consist of the stated steps with the materials set forth.

The invention will be explained further through the following examples.

DETAILED DESCRIPTION

Example 1

0.925 gram (1.55 mmoles) of rhenium VII sulfide and 0.5 gram of hydroquinone were dissolved in a mixture of 120 ml of acetic anhydride and 280 ml of acetic acid. Then at 80° C. within 2 hours under vigorous stirring there were dropped in 20.0 grams (0.155 mole) of 2-azido-propionic acid methyl ester.

The reaction proceeded with uniform development of nitrogen. After the end of the development of gas the mixture was allowed to further react for 20 hours at 80° C. and then the acetic acid and the excess acetic anhydride removed under reduced pressure. The residue was taken up in 100 ml of diethyl ether, the solution filtered, the filtrate evaporated and the residue chromatographed over a 20 cm high silica gel column with a mixture of low boiling petroleum ether and ethyl acetate in a volume ratio of 2:1 as mobile phase.

After the evaporation of the eluate there are obtained 15.7 grams (71% of theory) of analytically pure N-acetyl-2,3-dehydroalanine methyl ester,

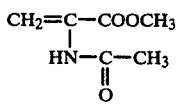

having a melting point of 52° C. (literature 52°–54° C.).

EXAMPLE 2

1.0 gram (5.84 mmole) of 2-azido-hexanoic acid methyl ester was dissolved in a mixture of 2 ml of acetic anhydride and 3 ml of acetic acid and treated with 5 mg of hydroquinone and 35 mg of rhenium VII sulfide. Then the solution was saturated with dry hydrogen chloride.

The reaction mixture was held for 2 hours at 80° C. under vigorous stirring and subsequently the product worked up in a manner analogous to Example 1. There were obtained 0.98 gram (91% of theory) of analytically pure N-acetyl-2,3-dehydro-norleucine methyl ester having a melting point of 49°–51° C.

| $C_9H_{15}NO_3$ (185, 22) | | | |
|---|---|---|---|
| | C | H | N |
| Calculated: | 58.36% | 8.16% | 7.56% |
| Found: | 58.18% | 8.25% | 7.48% |

$^1$H—NMR (CDCl$_3$):δ = 7.5 (s,1H) NH;
7.0 (t,1H) CH;
3.83 (s,3H) COOCH$_3$;
2.52 (q,2H) CH$_2$—CH=;
2.08 (s,3H) N—COCH$_3$;
1.49 (m,2H) CH$_3$—CH$_2$—CH$_2$;
0.94 ppm (t,3H) CH$_3$—CH$_2$.

Example 3

1.0 gram (4.56 mmole) of 2-azido-3-phenylpropionic acid ethyl ester was dissolved in a mixture of 1 ml of acetic anhydride and 4 ml of acetic acid and treated with 5 mg of hydroquinone and 27 mg of rhenium VII sulfide. Then the solution was saturated with dry halogen chloride.

The reaction mixture was held under vigorous stirring for 2.5 hours at 80° C. and subsequently worked up analogous to Example 1. There were obtained 0.96 grams (90% of theory) of analytically pure N-acetyl-2,3-dehydro-phenyl-alanine ethyl ester

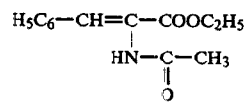

having a melting point of 96°–97.5° C. (literature 96°–98° C.).

| $C_{13}H_{15}NO_3$ (233, 267) | | | |
|---|---|---|---|
| | C | H | H |
| Calculated: | 66.94% | 6.48% | 6.01% |
| Found: | 66.77% | 6.62% | 5.72% |

$^1$H—NMR (CDCl$_3$):δ = 9.0 (s,1H) NH;
7.30–7.75 (m,5H) arom.-CH=;
4.26 (q,2H) COOCH$_2$;
1.32 (t,3H) COOCH$_2$—CH$_3$;
2.06 ppm (s,3H) CO—CH$_3$.

Example 4

1.0 gram (6.36 mmole) of 2-azido-3-methylbutyric acid methyl ester was dissolved in a mixture of 2 ml of acetic anhydride and 4 ml of acetic acid and treated with 5 mg of hydroquinone and 38 mg of rhenium VII sulfide. Then the solution was saturated with dry hydrogen chloride.

The reaction mixture was held at 80° C. with vigorous stirring for 2 hours and subsequently worked up analogous to Example 1. There was obtained 0.98 gram (90% of theory) of analytically pure N-acetyl-2,3-dehydrovaline methyl ester.

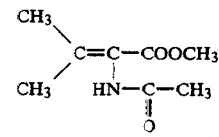

having a melting point of 93°–94° C. (Literature: 88°–89° C.).

| $C_8H_{13}NO_3$ (171,196) | | | |
|---|---|---|---|
| | C | H | N |
| Calculated: | 56.13% | 7.65% | 8.18% |
| Found: | 56.10% | 7.56% | 8.28% |

$^1$H—NMR (CDCl$_3$):δ = 7.55 (s,1H) NH;
3.72 (s,3H) COOCH$_3$;

2.15 (d,3H) CH$_3$
  ＼
   ＝
    ＼N;

2.06 (s,3H) CO—CH$_3$;

1.83 ppm (s,3H) CH₃ 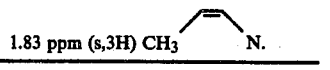

Example 5

1.0 gram (6.36 mmole) of 2-azido-3-methylbutyric acid methyl ester was dissolved in a mixture of 2 ml of acetic anhydride and 3 ml of acetic acid and treated with 10 mg of hydroquinone and 15.4 mg of rhenium VII oxide. Then the solution was saturated with dry hydrogen chloride.

The reaction mixture was held at 80° C. with vigorous stirring for two hours and subsequently worked up analogous to Example 1. There was obtained 0.97 gram (89% of the theory) of analytically pure N-acetyl-2,3-dehydro-valine methyl ester.

Example 6

1.0 gram (6.36 mmole) of 2azido-3-methylbutyric acid methyl ester was dissolved in a mixture of 2 ml of acetic anhydride and 3 ml of acetic acid and treated with 10 mg of hydroquinone and 1.5 mg of rhenium VII oxide. Then the solution was saturated with dry hydrogen chloride.

The reaction mixture was held at 80° C. under vigorous stirring for 2 hours and subsequently worked up analogous to Example 1. There were obtained 0.97 gram (89% of theory) of analytically pure N-acetyl-2,3-dehydro-valine methyl ester.

Example 7

1.0 gram (4.21 mmole) of 2-azido-3-phenylmercapto-propionic acid methyl ester was dissolved in a mixture of 1.5 ml of acetic anhydride and 3.5 ml of acetic acid and treated with 5 mg of hydroquinone and 25 mg of rhenium VII sulfide. Then the solution was saturated with dry hydrogen chloride.

The reaction mixture was held at 85° C. with vigorous stirring for 3 hours and subsequently worked up analogous to Example 1. There was obtained 0.82 gram (77% of theory) of N-acetyl-3-phenylmercapto-2,3-dehydro-alanine methyl ester.

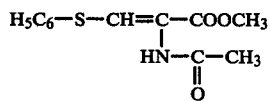

having a melting point of 103°–105° C.

| $C_{12}H_{13}NO_3S$ (251,304) | | | |
| --- | --- | --- | --- |
| C | H | N | S |
| Calculated: 57.35% | 5.21% | 5.57% | 12.76% |
| Found: 57.19% | 5.22% | 5.66% | 12.90% |

¹H—NMR (CDCl₃):δ = 8.06 (s,1H) NH;
7.2–7,6 (m,5H) arom.-CH=;
7.66 (s,1H) S—CH=;
3.78 (s,3H) COOCH₃;
2.18 ppm (s,3H) CO—CH₃.

The entire disclosure of German priority application No. P 3140227.5 is hereby incorporated by reference.

What is claimed is:

1. A process for the production of N-acetyl-2,3-dehydro-aminocarboxylic acid esters of the formula:

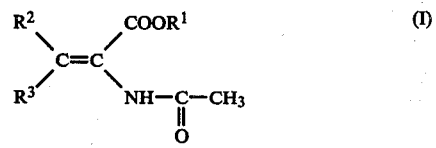

in which $R^1$ is a methyl or ethyl group, $R^2$ is hydrogen, or a methyl group and $R^3$ is hydrogen, an alkyl group having 1 to 6 carbon atoms, a phenyl group, an unsubstituted alkylmercapto group having 1 to 6 carbon atoms, a methoxycarbonylmethylmercapto group or a phenylmercapto group, comprising reacting a 2-azidocarboxylic acid ester of the formula:

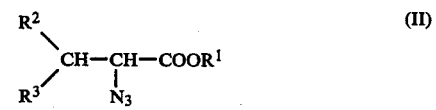

in the presence of rhenium VII sulfide, rhenium oxide, or a mixture of rhenium VII sulfide and rhenium VII oxide and at a temperature between 50° and 150° C. with a mixture of one part by volume of acetic anhydride and 1.5 to 5 parts by volume of acetic acid.

2. The process of claim 1 wherein the reaction is carried out in the simultaneous presence of dry hydrogen chloride.

3. The process of claim 2 wherein the reaction is carried out in the simultaneous presence of a polymerization inhibitor for radical polymerization.

4. The process of claim 1 wherein the reaction is carried out in the simultaneous presence of a polymerization inhibitor for radical polymerization.

5. The process of claim 4 where the polymerization inhibitor is hydroquinone or hydroquinone monomethyl ether.

6. The process of claim 4 wherein the rhenium VII sulfide, rhenium VII oxide or mixture of rhenium VII sulfide and rhenium VII oxide is employed in an amount of 0.01 to 10 mole percent based on the 2-azido-carboxylic acid ester of formula (II).

7. The process of claim 3 wherein the rhenium VII sulfide, rhenium VII oxide or mixture of rhenium VII sulfide and rhenium VII oxide is employed in an amount of 0.01 to 10 mole percent based on the 2-azido-carboxylic acid ester of formula (II).

8. The process of claim 2 wherein the rhenium VII sulfide, rhenium VII oxide or mixture of rhenium VII sulfide and rhenium VII oxide is employed in an amount of 0.01 to 10 mole percent based on the 2-azido-carboxylic acid ester of formula (II).

9. The process of claim 1 wherein the rhenium VII sulfide, rhenium VII oxide or mixture of rhenium VII sulfide and rhenium VII oxide is employed in an amount of 0.01 to 10 mole percent based on the 2-azido-carboxylic acid ester of formula (II).

10. The process of claim 9 wherein there is employed rhenium VII sulfide in an amount between 0.5 and 2 mole percent based on the 2-azido-carboxylic acid ester of formula (II).

11. The process of claim 8 wherein there is employed rhenium VII sulfide in an amount between 0.5 and 2 mole percent based on the 2-azido-carboxylic acid ester of formula (II).

12. The process of claim 9 wherein there is employed rhenium VII oxide in an amount between 0.05 and 1 mole percent.

13. The process of claim 8 wherein there is employed rhenium VII oxide in an amount between 0.05 and 1 mole percent.

14. The process of claim 1 wherein $R^3$ is hydrogen, an alkyl group having 1 to 6 carbon atoms, a phenyl group, a methyl mercapto group, a methoxycarbonylmethylmercapto group or a phenylmercapto group.

15. The process of claim 14 where $R^2$ is hydrogen and $R^3$ is hydrogen or alkyl of 1 to 3 carbon atoms.

16. The process of claim 15 where $R^3$ is hydrogen.

17. The process of claim 15 where $R^3$ is alkyl of 3 carbon atoms.

18. The process of claim 14 where $R^2$ is hydrogen and $R^3$ is phenyl.

19. The process of claim 14 where $R^2$ is methyl and $R^3$ is methyl.

20. The process of claim 14 where $R^2$ is hydrogen and $R^3$ is phenylmercapto.

* * * * *